US008406857B2

(12) United States Patent
Tsunoda et al.

(10) Patent No.: US 8,406,857 B2
(45) Date of Patent: Mar. 26, 2013

(54) APPARATUS FOR AND METHOD OF PROCESSING ULTRASONIC SIGNAL

(75) Inventors: Taro Tsunoda, Tokyo (JP); Kazuhiro Hirota, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1313 days.

(21) Appl. No.: 11/435,094

(22) Filed: May 17, 2006

(65) Prior Publication Data

US 2007/0016047 A1    Jan. 18, 2007

(30) Foreign Application Priority Data

May 20, 2005 (JP) .................................. 2005-148363

(51) Int. Cl.
*A61B 6/00* (2006.01)
(52) U.S. Cl. ....................................................... 600/476
(58) Field of Classification Search .................... 600/476
See application file for complete search history.

(56) References Cited

U.S. PATENT DOCUMENTS

| | | | |
|---|---|---|---|
| 5,524,628 A | | 6/1996 | Matsumoto et al. |
| 6,030,344 A * | | 2/2000 | Guracar et al. ............... 600/447 |
| 6,077,226 A | | 6/2000 | Washburn et al. |
| 6,200,268 B1 * | | 3/2001 | Vince et al. .................... 600/443 |
| 2004/0081340 A1 * | | 4/2004 | Hashimoto .................... 382/128 |
| 2004/0152983 A1 | | 8/2004 | Vince et al. |

FOREIGN PATENT DOCUMENTS

| | | |
|---|---|---|
| EP | 0 383 288 A1 | 8/1990 |
| JP | 2002-125971 A | 5/2002 |

OTHER PUBLICATIONS

Nair et al, Assessing spectral algorithms to predict atherosclerotic plaque composition with normalized and raw intravascular ultrasound data, Ultrasound in Medicine & Biology, vol. 27, Issue 10, Oct. 2001, pp. 1319-1331.*
European Search Report (in English) issued by The Hague on Oct. 6, 2006, in EP 06 01 0099.7.
Čakareski, Ž., et al., "*Statistics of the Integrated Backscatter Estimate from a Blood-Mimicking Fluid*", IEEE Transactions on Ultrasonics, Perroelectrics, and Frequency Control, Nov. 2001, pp. 1555-1567, vol. 48, No. 6, IEEE, New York, NY, US.
Picano, M.D., Eugenio, et al., "*The use of frequency histograms of ultrasonic backscatter amplitudes for detection of atherosclerosis in vitro*", Circulation, Nov. 1986, pp. 1093-1098, vol. 74, No. 5, Lippincott Williams & Wilkins, Hagerstown, MD, US.
Stähr, M.D., Peter M. et al., "*Discrimination of Early/Intermediate and Advanced/Complicated Coronary Plaque Types by Radiofrequency Intravascular Ultrasound Analysis*", The American Journal of Cardiology, Jul. 1, 2002, pp. 19-23, vol. 90, Excerpta Medica, Riverton, NJ, US.
Barzilai, Benico, et al., "*Quantitative Ultrasonic Characterization of the Nature of Atherosclerotic Plaques in Human Aorta*", Circulation Research, 1987, pp. 459-463, vol. 60, Lippincott Williams & Wilkins, Baltimore, MD, US.

(Continued)

*Primary Examiner* — Brian Casler
*Assistant Examiner* — Saurel J Selkin
(74) *Attorney, Agent, or Firm* — Buchanan Ingersoll & Rooney PC (57) ABSTRACT

RF signals in predetermined time regions are extracted respectively from a plurality of RF signals which are produced when an examinee is scanned by an ultrasonic wave, and respective IB values are calculated in the time regions. A variance value of the calculated IB values is calculated, and information based on the calculated variance value is output.

30 Claims, 10 Drawing Sheets

OTHER PUBLICATIONS

Bridal, S. Lori, et al., "*Relationship Between Ultrasonic Attenuation, Apparent Integrated Backscatter (30 to 50 MHz) and the Composition of Atherosclerotic Plaque*", Acoustical Imaging. Proceedings of the 23rd International Symposium on Acoustical Imaging, Boston, MA, Apr. 13-16, 1997, Proceedings of the International Symposium on Acoustical Imaging, Apr. 13, 1997, pp. 181-186, vol. 23, Plenum, New York, NY, US.

Spencer, T., et al., "*Characterisation of Atherosclerotic Plaque by Spectral Analysis of Intravascular Ultrasound: an In Vitro Methodology*", Ultrasound in Med & Biol., 1997, pp. 191-203, vol. 23, No. 2, Elsevier Science, Inc., New York, NY, US.

\* cited by examiner

APPARATUS FOR AND METHOD OF PROCESSING ULTRASONIC SIGNAL

FIELD OF THE INVENTION

The present invention generally relates to the field of tissue characterization. More specifically, the invention pertains to the filed of ultrasonic signal processing for tissue characterization using ultrasonic waves.

BACKGROUND DISCUSSION

Heretofore, there have widely been used ultrasonic diagnosing apparatus for diagnosing arteriosclerosis and performing a preoperative diagnosis and a postoperative check for coronary intervention using a dilatation catheter or a high-functionality catheter such as a stent or the like.

One example of ultrasonic diagnosing apparatus discussed below is intravascular ultrasound (IVUS) diagnosing apparatus. Generally, intravascular ultrasound diagnosing apparatus are constructed to include an ultrasonic probe that makes radial scans in an artery of the patient and receives an echo (reflected wave) reflected from a reflecting object in the artery. The echo signal is amplified and detected to convert the echo intensity into an image signal on a gray scale for thereby displaying a B-mode image.

B-mode images on the gray scale can display a large lipid in plaque deposited in the blood vessel. However, it is difficult for B-mode images to display a small lipid that may be present in an initial phase of plaque growth.

Since the rupture of vulnerable plaque in an artery is considered to be responsible for acute coronary syndromes such as an acute myocardial infarction, it is clinically desirable to diagnose plaque with a relatively high degree of accuracy. Specifically, when plaque in a blood vessel ruptures, the lipid contained in the plaque blows out into the blood vessel, leading to acute coronary syndromes. Therefore, an indication of the amount of lipid contained in plaque can serve as an important diagnostic marker.

Consequently, it is desirable in the art to develop ultrasonic diagnosing apparatus capable of sufficiently displaying tissue characters and allowing the user to easily determine whether or not plaque is relatively lipid-rich.

Efforts have been made with respect to ultrasonic diagnosing apparatus to increase the frequency of a transmitted ultrasonic signal in order to increase the resolution of the B-mode image or to analyze an RF signal obtained by receiving a reflected echo for tissue characterization. For example, a ROI (Region of Interest) is established in an analytic section, some parameters are calculated from the spectrum of an RF signal in the ROI, and tissue characters are displayed by a multivariable analysis.

It might be possible to attempt to display a smaller lipid by increasing the frequency for higher resolution. However, with this possibility, the range that can be diagnosed is limited because the depth that the ultrasonic wave can reach is reduced. Ultrasonic probes that are commercially available at present emit ultrasonic waves at a frequency of about 40 MHz and it is not clear at present whether high-frequency ultrasonic probes can generally be used for tissue characterization in blood vessels.

The process of analyzing an RF signal for tissue characterization is still under development at present and established procedures are not yet available. The process of displaying tissue characters by way of a multivariable analysis requires time-consuming calculations because the number of parameters involved is quite large as is the amount of analyzed data, and so this requires calibration of each ultrasonic probe to be used, a task not easy to perform.

SUMMARY

An apparatus for processing an ultrasonic signal comprises IB value calculating means for calculating IB values by extracting RF signals in predetermined time regions respectively from a plurality of RF signals which are produced when an examinee is scanned by an ultrasonic wave, variance value calculating means for calculating a variance value of the IB values calculated by the IB value calculating means, and output means for outputting information based on the variance value calculated by the variance value calculating means.

With the above arrangement, the existence of small foreign matter in an examinee can relatively easily determined in diagnosing tissue characters of the examinee with ultrasonic waves.

According to another aspect, an apparatus for processing an ultrasonic signal comprises IB value calculating means for extracting RF signals in predetermined time regions respectively from a plurality of RF signals produced when an examinee is scanned by an ultrasonic wave and calculating respective IB values in the time regions, linear average calculating means for calculating linear averages of the IB values calculated by the IB value calculating means in IB value groups with respect to mutually related time regions, variance value calculating means for calculating a variance value of the linear averages of the IB values calculated by the linear average calculating means, and output means for outputting information based on the variance value calculated by the variance value calculating means.

Another aspect pertains to a method of processing an ultrasonic signal comprising extracting RF signals in predetermined time regions respectively from a plurality of RF signals which are produced when an examinee is scanned by an ultrasonic wave, calculating respective IB values in the time regions, calculating a variance value of the calculated IB values, and outputting information based on the calculated variance value.

In accordance with another aspect, a method of processing an ultrasonic signal comprises scanning an examinee by an ultrasonic wave, extracting RF signals in predetermined time regions respectively from a plurality of RF signals which are produced by the scanning of the examinee by an ultrasonic wave, calculating respective IB values in the time regions, calculating linear averages of the calculated IB values in IB value groups with respect to mutually related time regions, calculating a variance value of an additive averages of the calculated IB values, and outputting information based on the calculated variance value.

Further aspect involve a control program for enabling a computer to perform the disclosed methods and a recording medium storing a control program for enabling a computer to perform the disclosed methods.

DETAILED DESCRIPTION

Configuration of an Ultrasonic Signal Processing System

Figure 1:
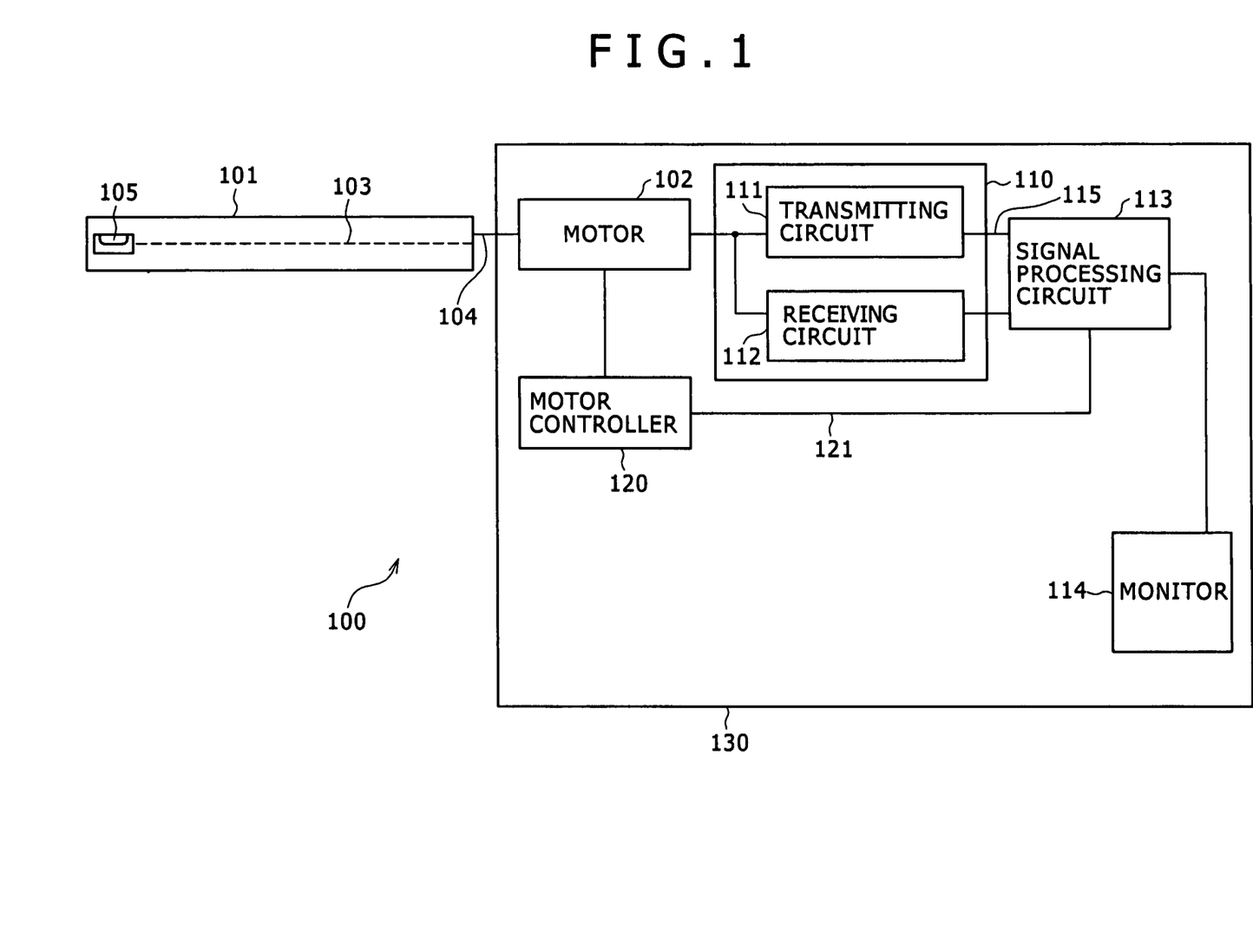
FIG. 1 is a block diagram of an ultrasonic signal processing system for performing an intravascular ultrasonic diagnosis in which the ultrasonic signal processing system incorporates an ultrasonic signal processing apparatus according to a first embodiment.

FIG. 1 schematically illustrates an ultrasonic signal processing system 100 for performing an intravascular ultrasonic diagnosis. The ultrasonic signal processing system 100 incorporates an ultrasonic signal processing apparatus 130 according to one disclosed embodiment.

As shown in FIG. 1, the ultrasonic signal processing system 100 for performing intravascular ultrasonic diagnosis comprises a catheter 101 and an ultrasonic signal processing apparatus 130.

The catheter 101 has an ultrasonic transducer 105 disposed in its tip end. When the catheter 101 is inserted in a blood vessel, the ultrasonic transducer 105 transmits an ultrasonic wave in the cross-sectional direction of the blood vessel based on a pulse signal sent from an ultrasonic signal transmitter/receiver 110 through signal lines 104, 103, receives a reflected wave (echo) of the transmitted ultrasonic wave, and sends an ultrasonic signal (as an electric signal) representative of the echo through the signal lines 104, 103 to the ultrasonic signal transmitter/receiver 110.

The ultrasonic signal processing apparatus 130 includes a motor 102, the ultrasonic signal transmitter/receiver 110, a signal processing circuit 113, a monitor 114, and a motor controller 120.

The ultrasonic transducer 105 is rotatably mounted in the catheter 101 for being rotated by a motor 102 that is detachably connected to the catheter 101. When the ultrasonic transducer 105 is rotated circumferentially in the blood vessel, it can detect an ultrasonic echo signal to be used for tissue characterization of the blood vessel in the circumferential direction at a certain cross section of the blood vessel. The operation of the motor 102 is controlled by the motor controller 120 based on a control signal that is sent from the signal processing circuit 113 through a signal line 121.

The ultrasonic signal transmitter/receiver 110 has a transmitting circuit 111 and a receiving circuit 112. The transmitting circuit 111 supplies a pulse signal to the ultrasonic transducer 105 in the catheter 101 based on a control signal that is sent from the signal processing circuit 113 through a signal line 115.

The receiving circuit 112 receives an ultrasonic signal sent from the ultrasonic transducer 105 in the catheter 101. The ultrasonic signal received by the receiving 112 is sent to the signal processing circuit 113, which processes the ultrasonic signal and outputs the processed ultrasonic signal to the monitor 114.

The monitor 114 displays images based on various signals output from the signal processing circuit 113. The signal processing circuit 113 is capable of outputting an RF signal, i.e., a signal produced by converting an ultrasonic signal into a digital signal, and a B-mode signal used to generate a B-mode image, to the monitor 114. The signal processing circuit 113 is also capable of processing such an RF signal and a B-mode signal for performing an intravascular ultrasonic diagnosis and outputting the processed signals to the monitor 114.

Operation of the Catheter In an Intravascular Ultrasonic Diagnosis

Figure 2:
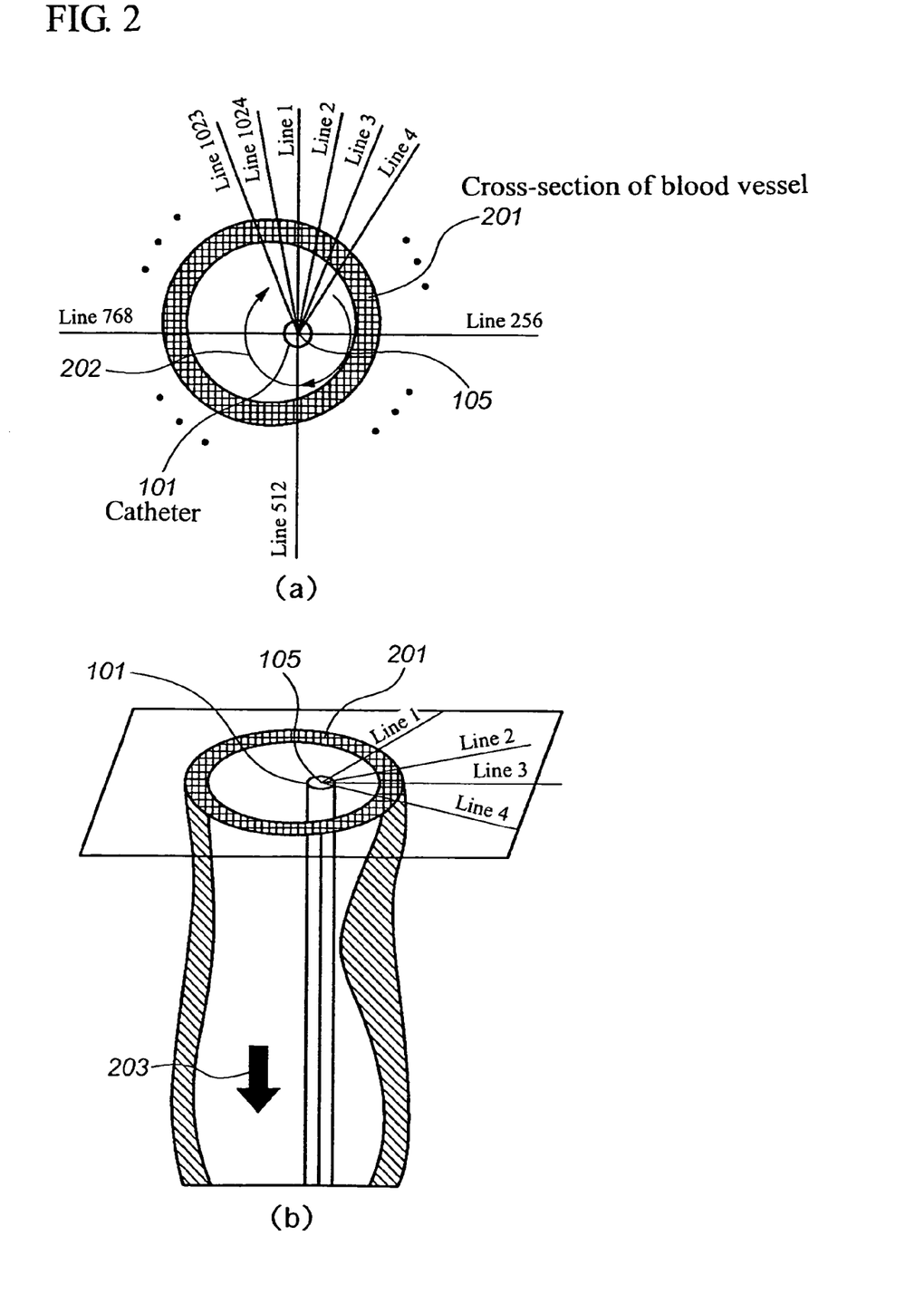
FIGS. 2(a) and 2(b) are somewhat schematic views illustrating the manner in which a catheter operates in an intravascular ultrasonic diagnosis.

FIGS. 2(a) and 2(b) illustrate the manner in which the catheter 101 operates in an intravascular ultrasonic diagnosis. FIG. 2(a) is a cross-sectional view of a blood vessel with the catheter 101 inserted therein, and FIG. 2(b) is a perspective view of the blood vessel with the catheter 101 inserted therein.

As seen in FIG. 2(a), the ultrasonic transducer 105 mounted in the tip of the catheter 101 is rotated by the motor (the motor 102 shown in FIG. 1) in the direction indicated by the arrow 202.

The ultrasonic transducer 105 transmits and receives an ultrasonic wave at each of the angular positions thereof in the blood vessel. Specifically, the ultrasonic transducer 105 transmits an ultrasonic wave along respective radial lines 1, 2, ..., 1024 at different angular positions as illustrated by way of example in FIG. 2(a). While the ultrasonic transducer 105 is rotating 360 degree in the blood vessel cross section 201, it intermittently transmits and receives an ultrasonic wave a total of 1024 times. The number of times that the ultrasonic transducer 105 transmits and receives an ultrasonic wave while it is rotating 360 degree is not limited to 1024 as this is merely described by way of example. The number of times the ultrasonic transducer 105 transmits and receives an ultrasonic wave while it is rotating 360 degree may thus be selected as desired.

The ultrasonic transducer 105 transmits and receives an ultrasonic wave along the radial lines 1, 2, ..., 1024 while it is traveling in the direction indicated by the arrow 203 (see FIG. 2(b)) in the blood vessel. The scanning process in which ultrasonic transducer 105 repeatedly transmits and receives an ultrasonic wave in each blood vessel cross section while traveling in the direction indicated by the arrow 203 is referred to as the "radial scanning process."

General Ultrasonic Signal Processing

Figure 3:
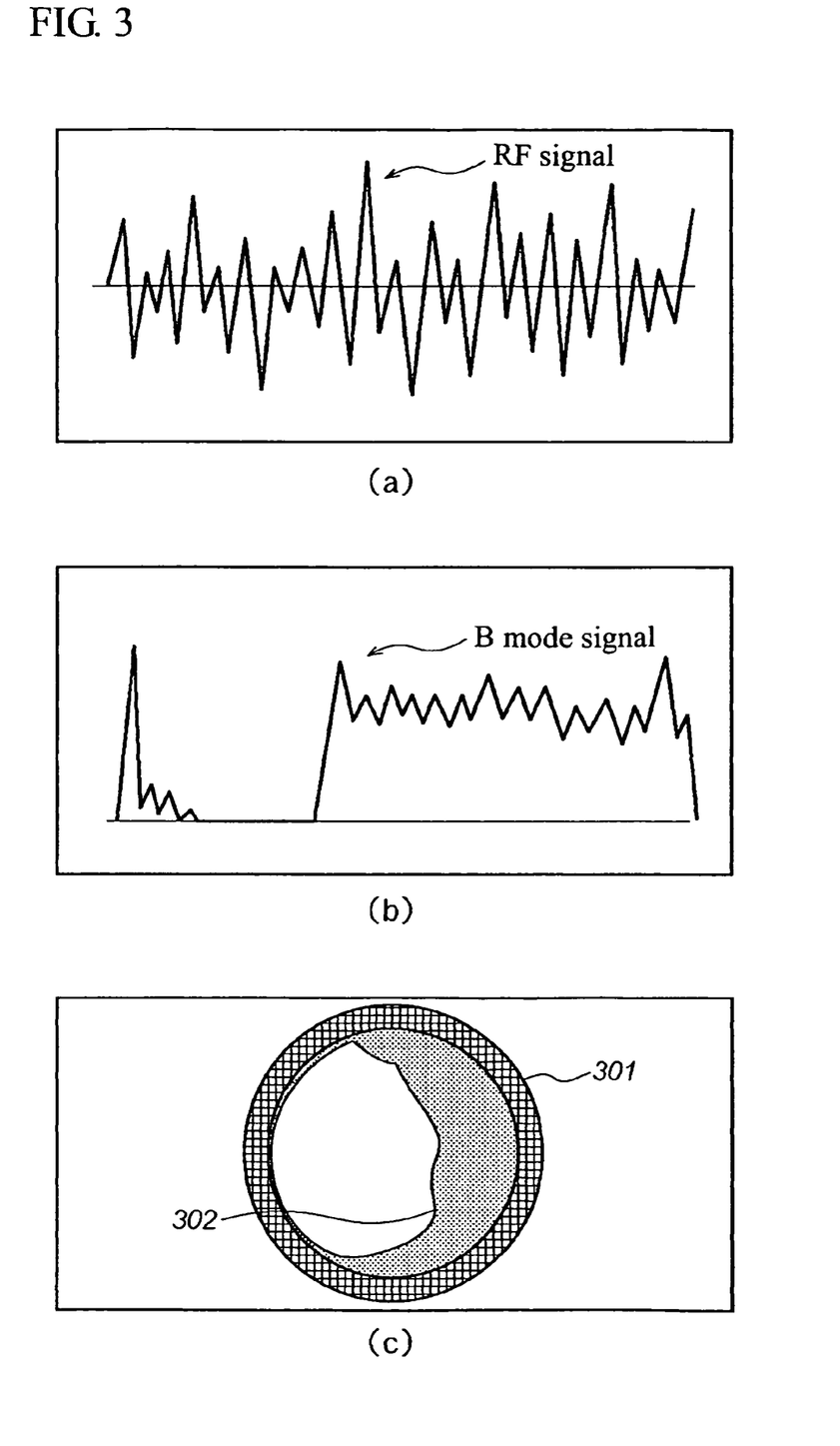
FIGS. 3(a)-(c) are diagrams illustrating a general process for processing an ultrasonic signal during intravascular ultrasonic diagnosis.

A general process of processing an ultrasonic signal in the intravascular ultrasonic diagnosis will be described below with reference to FIGS. 3(a)-(c). FIG. 3(a) shows an RF signal representing a reflected ultrasonic wave that is received by the ultrasonic transducer 105. In FIG. 3(a), the horizontal axis represents time and the vertical axis the intensity of the RF signal.

FIG. 3(b) shows a B-mode signal that is produced when the RF signal is amplified and detected by the signal processing circuit 113 to convert the echo intensity into an image signal on a gray scale. In FIG. 3(b), the horizontal axis represents time and the vertical axis the gray scale. The B-mode signal shown in FIG. 3(b) represents a signal along one line in the blood vessel cross section 201.

FIG. 3(c) shows a B-mode image that is generated from a circumferential array of B-mode signals along the lines 1 through 1024 in the blood vessel cross section 201. In FIG. 3(c) the B-mode image includes a blood vessel 301 and plaque 302 deposited in the blood vessel 301.

Arrangement of the Signal Processing Circuit

Figure 5:
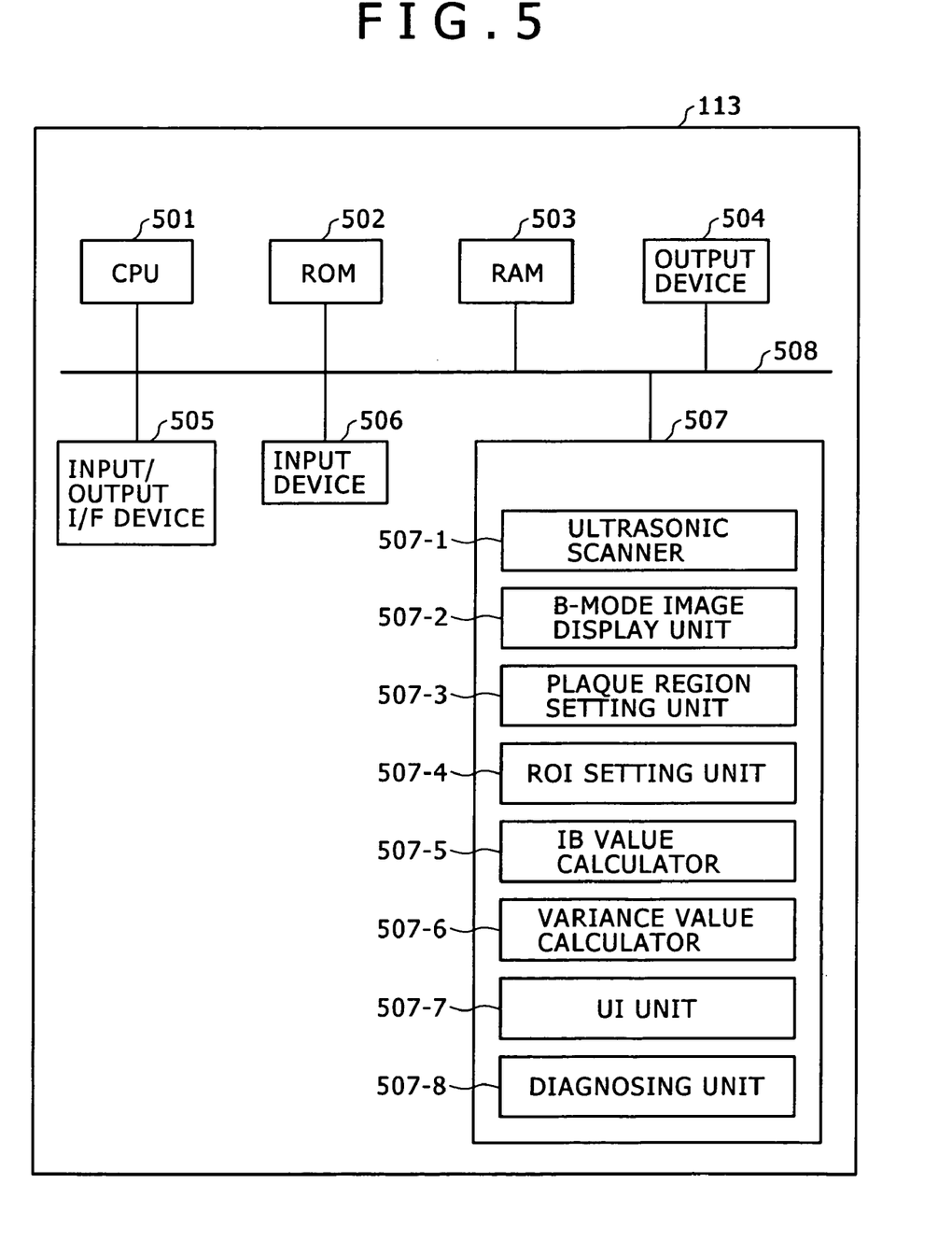
FIG. 5 is a block diagram of the ultrasonic signal processing apparatus according to the first embodiment.

An arrangement of the signal processing circuit 113 will be described below with reference to FIG. 5. FIG. 5 shows in block form the arrangement of the signal processing circuit 113 according to this embodiment.

As shown in FIG. 5, the signal processing circuit 113 has a central processing unit (CPU) 501, a control memory (ROM) 502, and a memory (RAM) 503. The signal processing circuit 113 also has an output device 504 connected to the monitor 114 for outputting a signal such as a B-mode image signal to the monitor 114, an input/output interface (I/F) device 505 for sending signals to and receiving signals from the transmission wave circuit 111 and the motor controller 120, an input device 506 including a track ball, a mouse, a keyboard, etc. for entering signals, a storage device 507 such as a HDD or the like, and a bus 508.

Control programs for performing ultrasonic signal processing functions according to this embodiment and data used by the control program are stored in the storage device 507 (representing functions 507-1 through 507-8 to be described in more detail later). The control programs and data are loaded through the bus 508 into the memory 503 under the control of the CPU 501, and executed by the CPU 501.

Figure 6:
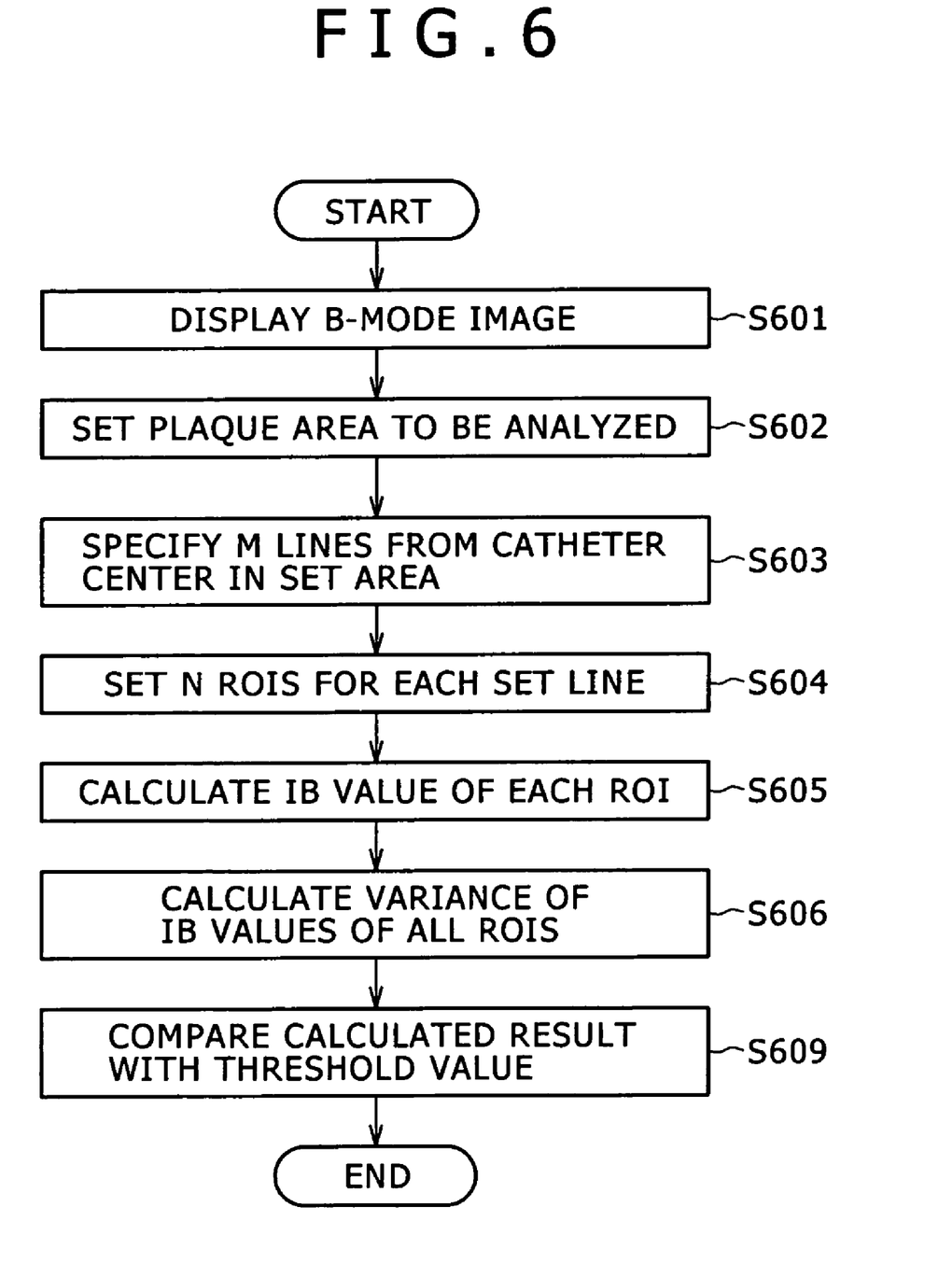
FIG. 6 is a flowchart of a processing sequence of the ultrasonic signal processing apparatus according to the first embodiment for performing an intravascular ultrasonic diagnosis.

Processing of the Ultrasonic Signal Processing Apparatus for an Intravascular Ultrasound Diagnosing FIG. 6 shows a processing sequence of the ultrasonic signal processing apparatus 130 according to this embodiment for performing an intravascular ultrasonic diagnosis. The processing sequence of the ultrasonic signal processing apparatus 130 for performing an intravascular ultrasonic diagnosis will be described below with reference to FIG. 6. The processing sequence will be described below while referring to a B-mode image shown in FIG. 4. The processing sequence shown in FIG. 6 is premised on the ultrasonic scanner 507-1 having been operated and the radial scanning process having been completed.

In step S601 shown in FIG. 6, a B-mode image display unit 507-2 operates to display a B-mode image 400 (see FIG. 4) on the monitor 114. In step S602, a plaque region setting unit 507-3 recognizes a plaque area 401 that is designated by the user based on the displayed B-mode image 400, and sets the plaque area 401 in an IB (integrated backscatter) value calculator 507-5.

For allowing the user to make various designations or indications on the B-mode image displayed on the monitor 114, it is assumed that a UI (User Interface) unit 507-7 has operated to allow the user to make such various designations or indications through the input device 506.

Figure 4:
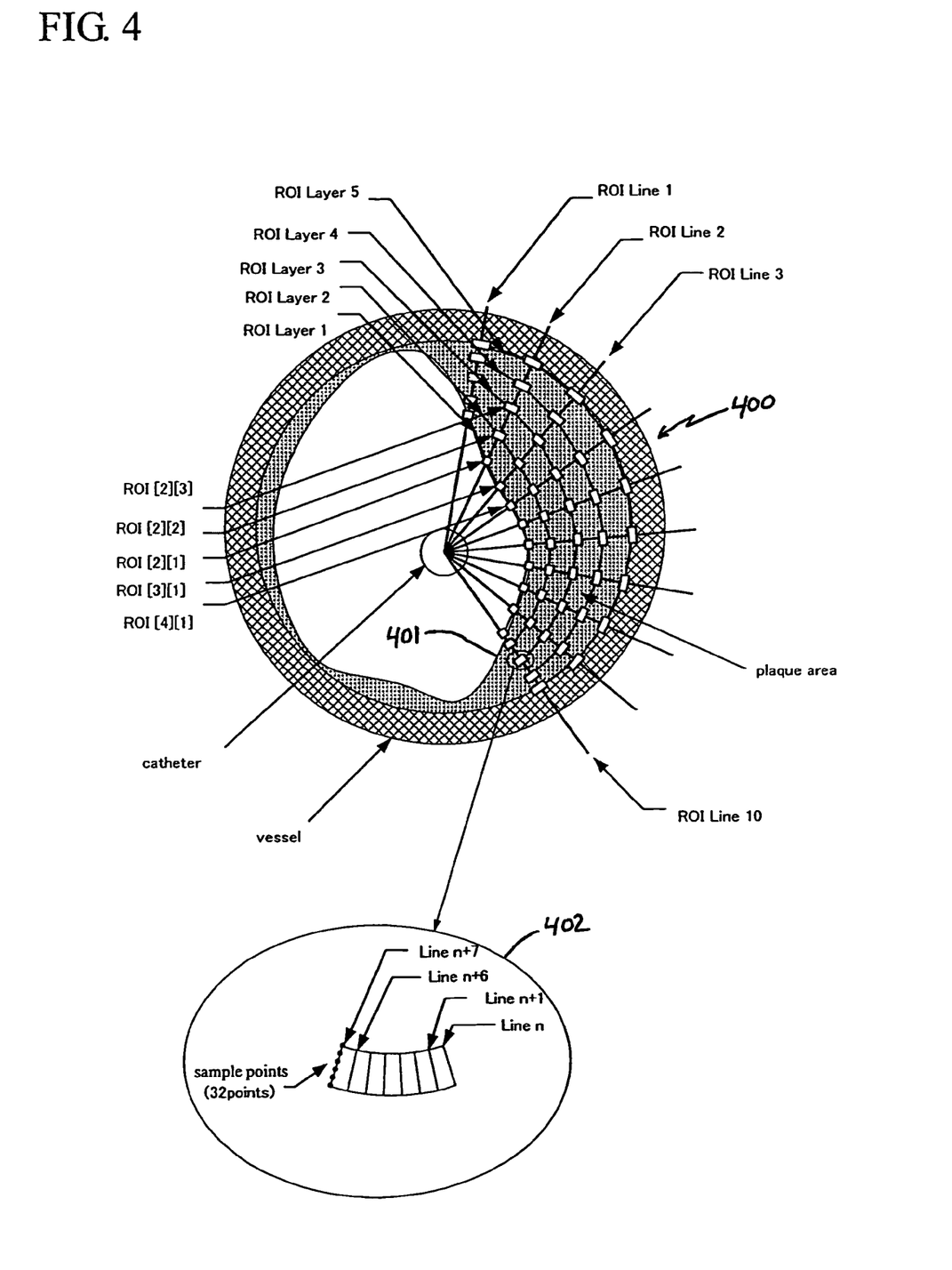
FIG. 4 is a diagram showing a B-mode image.

In step S603, the user designates M ROI Lines (lines for specifying a direction in which to array ROIs) from the center of the catheter 101 within the designated plaque area 401.

In step S604, the user designates N ROIs for each of the designated M ROI Lines. A ROI setting unit 507-4 recognizes the designated ROIs and sets the recognized ROIs in the IB value calculator 507-5.

FIG. 4 shows that 10 ROI Lines (arranged circumferentially) multiplied by 5 layers (arranged radially)=50 ROIs are set in the plaque area 401. For illustrative purposes, the 10 ROI Lines are referred to as ROI Line 1, ROI Line 2, . . . , ROI Line 10, respectively. Of the ROIs designated on the ROI Lines, a ROI group that is closest to the catheter 101 is referred to as ROI Layer 1. ROI groups that are positioned progressively farther from the catheter 101 are referred to as ROI Layer 2, ROI Layer 3, ROI Layer 4, ROI Layer 5.

Each ROI is defined by a ROI Line and a ROI Layer. For example, a ROI on ROI Line 2 in ROI Layer 1 is defined as ROI [2] [1], and a ROI on ROI Line 3 in ROI Layer 1 is defined as ROI [3] [1].

As shown in FIG. 4, a ROI has a certain radial width and a certain circumferential width. It is assumed in the present embodiment that all the 50 ROIs have the same size. The radial width corresponds to the time region of the RF signal. An encircled region 402 is illustrative of the size of each ROI. According to the present embodiment, one ROI contains 8 lines, 32 samples.

If an ultrasonic signal is converted into a digital signal at a frequency of 240 MHz, then the 32 samples correspond to about 0.1 mm as calculated according to $1.530 \times 10^6$ (mm/sec)/2 (reciprocated)$\times 32$ (samples)/$240 \times 10^6$ (samples/sec)= 0.102 mm. If the ultrasonic transducer 105 intermittently transmits and receives an ultrasonic wave a total of 1024 times per rotation, then the eight lines correspond to 2.8 degree as calculated according to 1024 (lines/rotation)$\times 360$ (degree/rotation) =2.8 degree.

As the frequency of the ultrasonic wave emitted by the ultrasonic transducer is higher, a more detailed analysis, i.e., an analysis at a higher resolution, is possible, and a smaller lipid in the plaque can be detected. Therefore, the ultrasonic wave emitted by the ultrasonic transducer should preferably have a frequency of 50 MHz or higher.

In step S605 shown in FIG. 6, the IB value calculator 507-5 operates to calculate an IB (Integrated Backscatter) value for each ROI. In the present embodiment, the IB value calculator 507-5 calculates the IB value (total) of the eight lines in each ROI.

Specifically, the IB value calculator 507-5 calculates an FFT (fast Fourier transform) of an RF signal that is produced by converting an ultrasonic signal into a digital signal, thereby determining a power spectrum P(f) which is a function of the frequency f. If it is assumed that the ultrasonic transducer which is used has a bandwidth [f1, f2], then an IB value for each ROI is determined by integrating the power spectrum in the range from f1 to f2, dividing the integral by the number of samples (32 samples in the present embodiment) of the RF signal, and standardizing.

Specifically, the IB value on a line m in a ROI is calculated according to the following equation:

$$IB_{Line\ m} = \int_{f1}^{f2} P_{Line\ m}(f)/32\ (32\ \text{is the number of samples})$$

By determining linear average of the IB values on all the lines in the ROI, the IB value for each ROI is determined. Specifically, the IB value for ROI [M] [N] is calculated as follows:

$$IB_{ROI[M][N]} = \Sigma IB_{Line\ m}/8\ (8\ \text{is the number of lines})$$

In step S606, a variance value calculator 507-6 operates to calculate a variance of the IB values for all the ROIs according to the following equation:

$$\sigma = \sum_M \sum_N (IB_{ROI(M)(N)} - \text{average}(IB_{ROI(M)(N)}))^2 / (10 \times 5 - 1)$$

(10 is the number of ROI Lines, and 5 is the number of ROI Layers)

In the above equation, $$\text{average}(IB_{ROI(M)(N)}) = \sum_{M}\sum_{N} IB_{ROI(M)(N)} / (10 \times 5)$$

(10 is the number of ROI Lines, and 5 is the number of ROI Layers)

In step S609, a diagnosing unit 507-8 operates to compare the calculated variance value with a predetermined threshold value (e.g., 32). If the calculated variance value is greater than the threshold value, the diagnosing unit 507-8 judges that the plaque 401 is a lipid rich plaque, and displays "Lipid" or the like in the B-mode image.

According to the above embodiment, as described above, the variance value of the IB values of the ROIs in the plaque area is calculated and compared with the threshold value to determine whether the plaque to be analyzed is lipid rich or not. It is also possible to determine whether the plaque to be analyzed is stable or unstable. According to the above embodiment, furthermore, the processing sequence has a shorter calculation time for an easier analysis than the conventional process.

In the first embodiment described above, after the IB values for the ROIs have been calculated, the variance value of the IB values for all the ROIs is calculated and compared with the threshold value to determine whether or not the plaque to be analyzed is lipid rich. However, the present invention is not limited to this embodiment.

According to a second embodiment, a linear average of IB values for a group of every M ROIs in the same ROI layer is determined, and a variance value of the average IB value is calculated and compared with a threshold value to determine whether or not the plaque to be analyzed is lipid rich.

Figure 7:
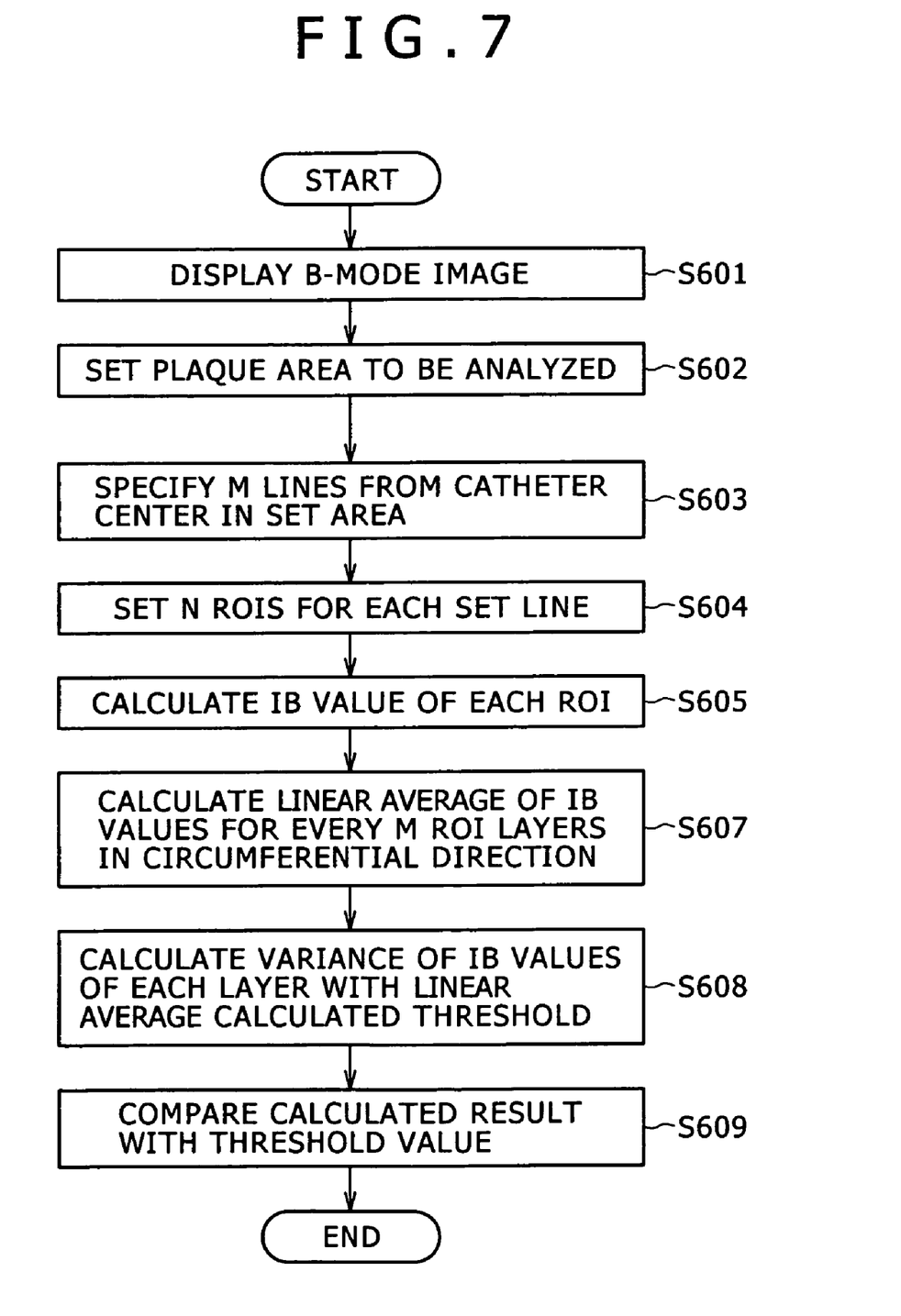
FIG. 7 is a flowchart of a processing sequence of an ultrasonic signal processing apparatus according to a second embodiment for performing an intravascular ultrasonic diagnosis.

FIG. 7 shows a processing sequence of an ultrasonic signal processing apparatus according to a second embodiment of the present invention. Of the processing sequence shown in FIG. 7, steps S601 through S605 are identical to those shown in FIG. 6, and will not be described in detail again.

In step S607, a linear average of IB values of every M ROIs in the ROI layer N is determined. Specifically, the linear average is calculated according to the equation:

$$IB_{ROILayerN} = \sum_{M} IB_{ROI(M)(N)} / 10$$

(10 is the number of ROI Lines)

In step S608, a variance value of the average IB values of each ROI layer is calculated as follows:

$$\sigma = \sum_{N} (IB_{ROILayerN} - \text{average}(IB_{ROILayerN}))^2 / (5-1)$$

(5 is the number of ROI Layers)
In the above equation, $$\text{average}(IB_{ROILayerN}) = \sum_{N} IB_{ROILayerN} / 5$$

(5 is the number of ROI Layers)

In step S609, the diagnosing unit 507-8 compares the variance value determined in step S608 with a predetermined threshold value. If the variance value is greater than the threshold value, the diagnosing unit 507-8 judges that the plaque 401 is a lipid rich plaque, and displays "Lipid" or the like in the B-mode image.

In the first and second embodiments, processes for the user to designate or specify a ROI have not been described. However, the ultrasonic signal processing apparatus according to the present invention allows a ROI to be designated or specified by any of various processes. A ROI may be specified by specifying the position of a ROI Line and specifying the position of the ROI on the specified ROI Line. A process of specifying the position of a ROI Line and a process of specifying the position of the ROI on the specified ROI Line is described below.

Figure 8:
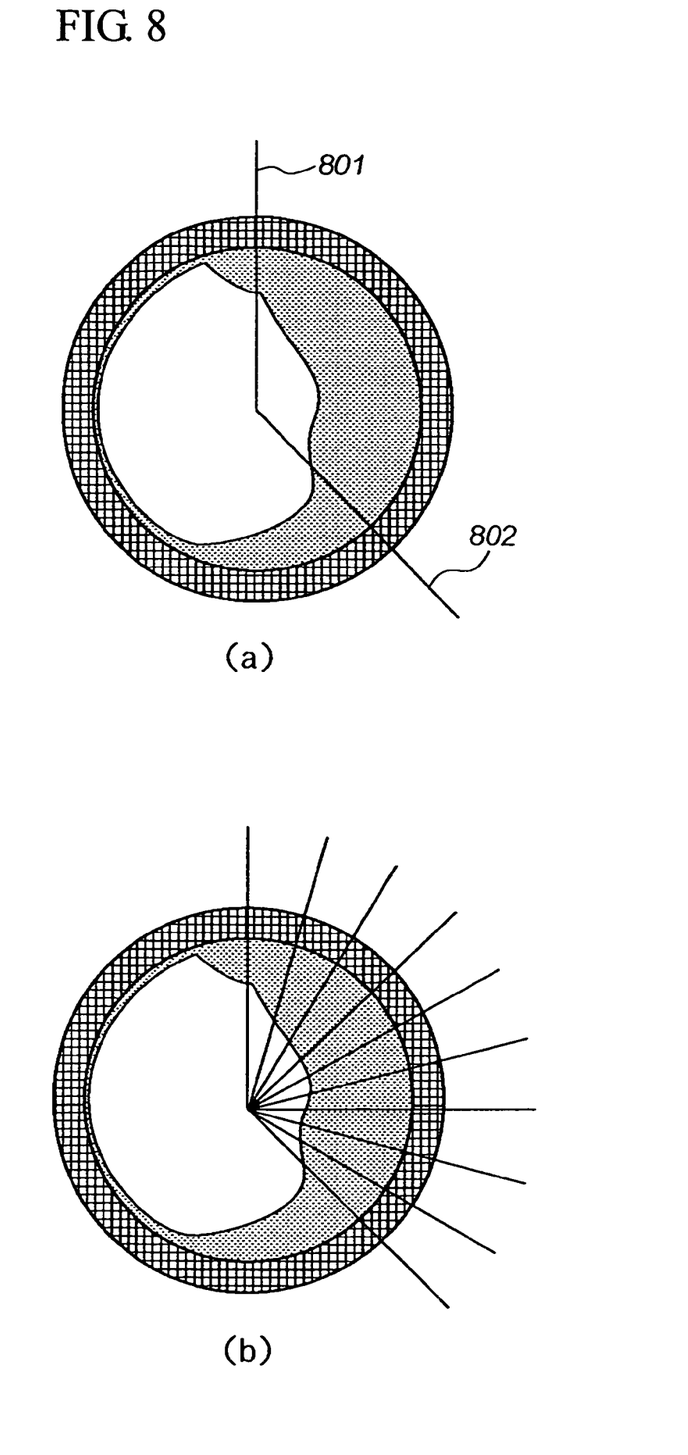
FIGS. 8(a) and 8(b) are cross-sectional views illustrating a process of specifying region of interest (ROI) lines.

Process of Specifying the Position of a ROI Line:

FIGS. 8(*a*) and 8(*b*) show by way of example a process of specifying the position of a ROI Line. According to the illustrated process, the number of ROI Lines to be specified is predetermined, and the user specifies only a range in which ROI Lines are positioned. Specifically, as shown in FIG. 8(*a*), when the user specifies a ROI Line 801 and a ROI Line 802, eight equally spaced radial lines are automatically specified between the ROI Line 801 and the ROI Line 802, as shown in FIG. 8(*b*).

Since the user specifies only a range in which ROI Lines are positioned, the user can specify ROI Lines quickly without a lot of trouble.

Figure 9:
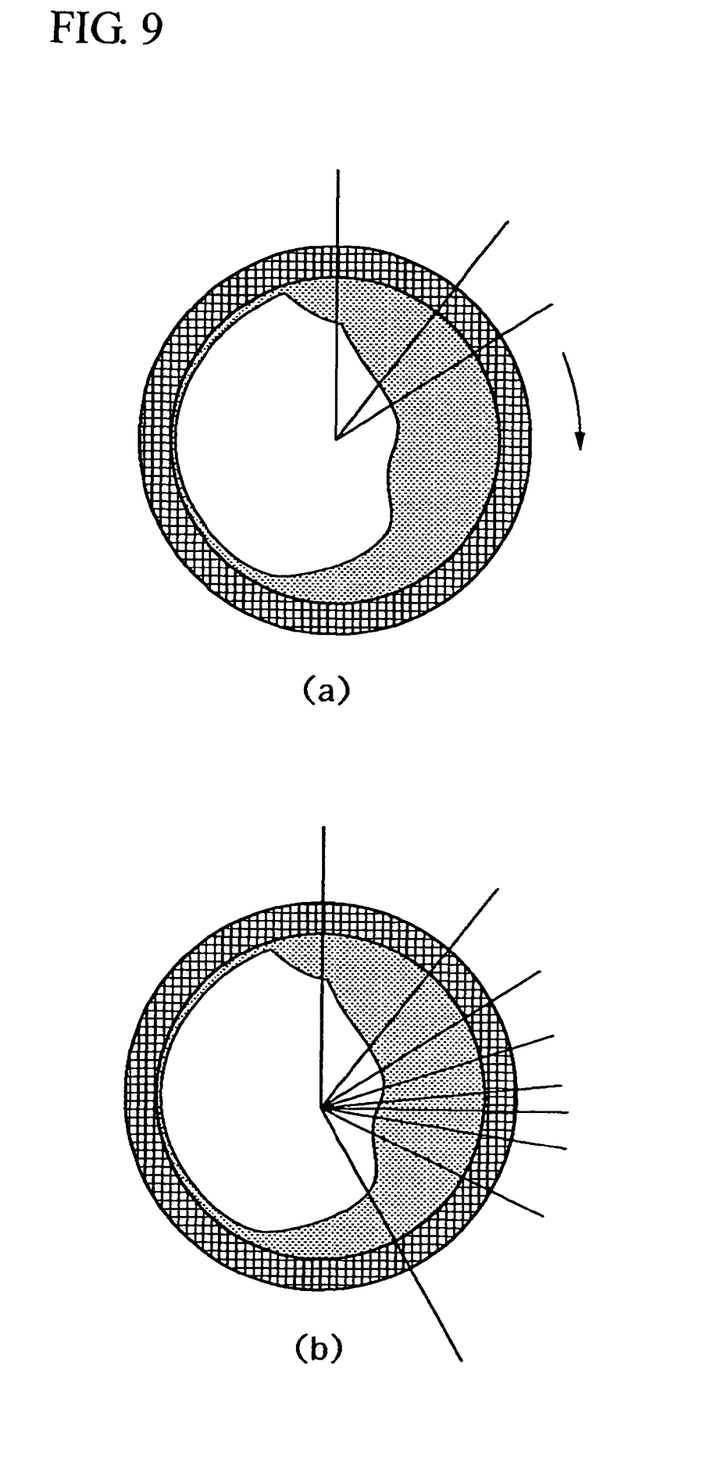
FIGS. 9(a) and 9(b) are cross-sectional views illustrating another process of specifying ROI lines.

FIGS. 9(*a*) and 9(*b*) show by way of example another process of specifying the position of a ROI Line. According to this other process, the user specifies all ROI Lines that the user wants to be specified. Since the user can specify any desired number of ROI Lines at any desired positions while seeing a B-mode image, it is expected that the user can conduct a diagnosis with increased latitude.

Process of Specifying the Position of a ROI on a Specified ROI Line:

A process of specifying the position of a ROI on a specified ROI Line will be described below. It is assumed that the process is performed when ROI Lines have been specified according to the specifying process shown in, for example, FIGS. 8(*a*) and 8(*b*). However, the process may also be applicable when ROI Lines have been specified according to the specifying process shown in, for instance, FIGS. 9(*a*) and 9(*b*).

Figure 10:
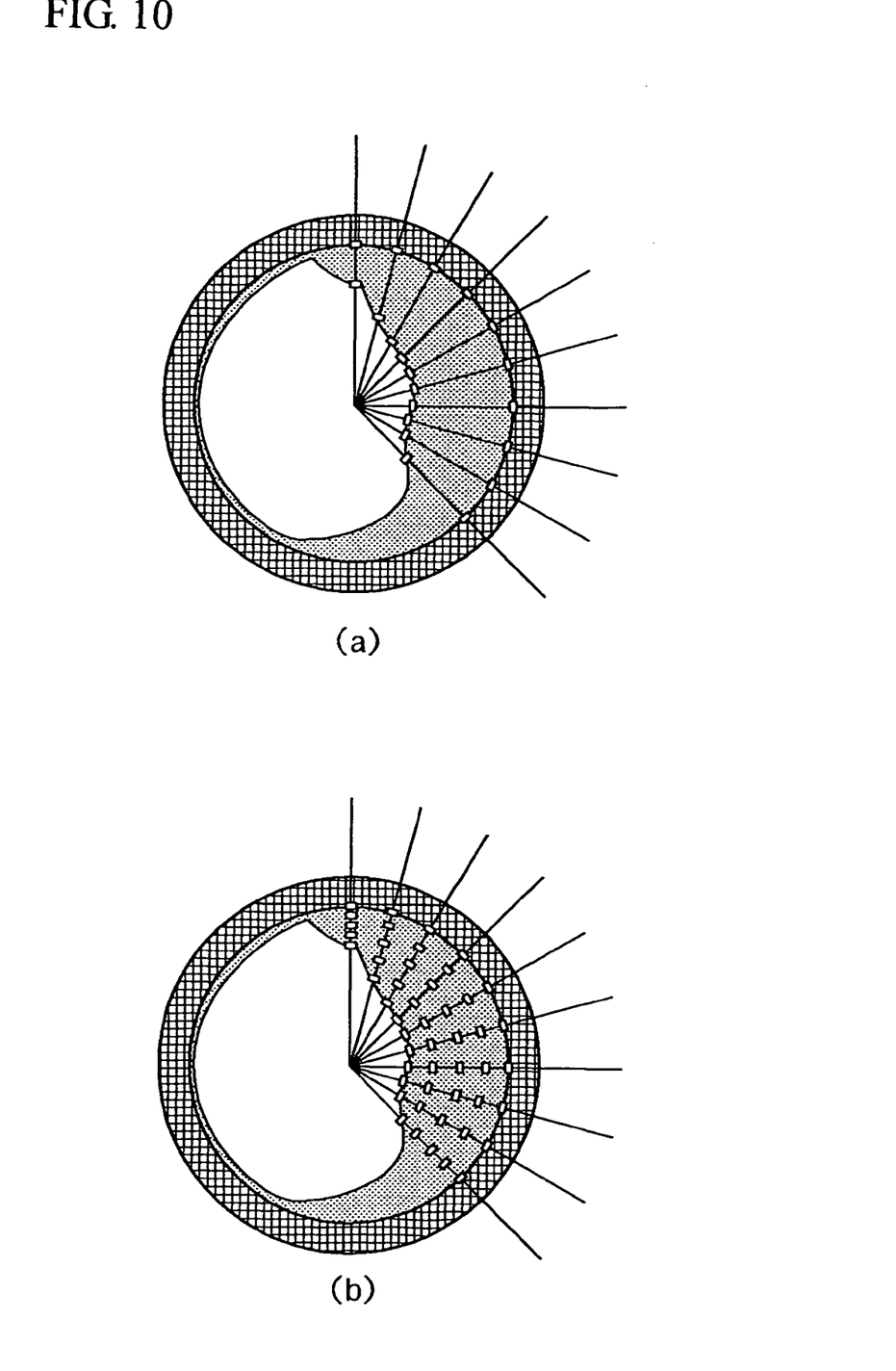
FIGS. 10(a) and 10(b) are cross-sectional views illustrative of a process of placing regions of interest (ROIs) on ROI lines.

FIGS. 10(*a*) and 10(*b*) show by way of example a process of specifying the position of a ROI on a specified ROI Line. According to the process, it is assumed that the number of ROIs to be placed on each ROI Line is predetermined (5 ROIs/ROI Line), and the user specifies a range in which ROIs are positioned on the ROI Lines. Specifically, as shown in FIG. 10(*a*), the user places ROI [1] [1], ROI [1] [5], ..., ROI [10] [1], ROI [10] [5] in order to specify a range in which to position ROIs on ROI Lines 1 through 10. Then, as shown in FIG. 10(*b*), three new ROIs (e.g., ROIs [1] [2] through [1] [4]) are automatically placed at equal intervals between the specified ROIs on each ROI Line (e.g., ROI [1] [1] and ROI [1] [5] on ROI Line 1).

Since the user can specify any desired range in which to place ROIs on ROI Lines, it is expected that the user can specify the positions of ROIs quickly without a lot of trouble.

The principles and preferred embodiments have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An apparatus for processing an ultrasonic signal, comprising:
a signal processing circuit configured to calculate integrated backscatter values by extracting radio-frequency signals in predetermined time regions respectively from a plurality of radio-frequency signals which are produced when an examinee is scanned by an ultrasonic wave;
the signal processing circuit being configured to calculate a variance value of the integrated backscatter values;
wherein the examinee is a plaque in a blood vessel; and
the signal processing circuit is further configured to compare the variance value with a predetermined threshold value and to judge that the examinee is a lipid rich plaque when the variance value is greater than the predetermined threshold value.

2. The apparatus according to claim 1, further comprising:
a display configured to display a B-mode image of the examinee which is generated based on the radio-frequency signals; and
the signal processing circuit is configured to set regions of interest at given positions in the B-mode image displayed by the display;
the time regions being determined depending on positions of the regions of interest.

3. The apparatus according to claim 2, wherein
the signal processing circuit is configured to set a plurality of lines specifying a direction in which to array the regions of interest in the B-mode image; and
the signal processing circuit is configured to array the same number of regions of interest on each of the lines.

4. The apparatus according to claim 3, wherein each of the radio-frequency signals includes a signal produced when an ultrasonic transducer mounted on a catheter makes a radial scan in the examinee, and the signal processing circuit is configured to set the lines as equally spaced radial lines from a central position of the catheter in the B-mode image.

5. The apparatus according to claim 4, wherein the signal processing circuit sets the lines at equally spaced intervals between two lines specified by a user and extending radially from the central position of the catheter in the B-mode image.

6. The apparatus according to claim 4, wherein the signal processing circuit arrays the regions of interest at equally spaced intervals between two regions of interest specified by a user on each of the lines.

7. The apparatus according to claim 1, wherein the ultrasonic wave has a frequency of at least 50 MHz.

8. The apparatus according to claim 7, wherein the signal processing circuit arrays the regions of interest at equally spaced intervals between two regions of interest specified by a user on each of the lines.

9. An apparatus for processing an ultrasonic signal, comprising:
a signal processing circuit configured to extract radio-frequency signals in predetermined time regions respectively from a plurality of radio-frequency signals produced when an examinee is scanned by an ultrasonic wave and calculate respective integrated backscatter values in the time regions;
the signal processing circuit being configured to calculate linear averages of the integrated backscatter values in integrated backscatter value groups with respect to mutually related time regions;
the signal processing circuit being configured to calculate a variance value of the linear averages of the integrated backscatter values
wherein the examinee is a plaque in a blood vessel; and
the signal processing circuit is further configured to compare the variance value with a predetermined threshold value and to judge that the examinee is a lipid rich plaque when the variance value is greater than the predetermined threshold value.

10. The apparatus according to claim 9, further comprising:
a display configured to display a B-mode image of the examinee which is generated based on the radio-frequency signals; and
the signal processing unit is configured to set regions of interest at given positions in the B-mode image displayed by the display;
the time regions being determined depending on positions of the regions of interest.

11. The apparatus according to claim 10, wherein
the signal processing circuit is configured to set a plurality of lines specifying a direction in which to array the regions of interest in the B-mode image; and
the signal processing circuit is configured to array the same number of regions of interest on each of the lines.

12. The apparatus according to claim 11, wherein each of the radio-frequency signals includes a signal produced when an ultrasonic transducer mounted on a catheter makes a radial scan in the examinee, and the signal processing circuit is configured to set the lines as equally spaced radial lines from a central position of the catheter in the B-mode image.

13. The apparatus according to claim 12, wherein each of the mutually related time regions comprises a time region corresponding to a predetermined region of interest as counted from the central position of the catheter in the B-mode image on one of the lines.

14. The apparatus according to claim 12, wherein the signal processing circuit sets the lines at equally spaced intervals between two lines specified by a user and extending radially from the central position of the catheter in the B-mode image.

15. The apparatus according to claim 9, wherein the ultrasonic wave has a frequency of at least 50 MHz.

16. A method of processing an ultrasonic signal, comprising:
extracting radio-frequency signals in predetermined time regions respectively from a plurality of radio-frequency signals which are produced when an examinee, which is a plaque in a blood vessel, is scanned by an ultrasonic wave;
calculating respective integrated backscatter values in the time regions;
calculating a variance value of the calculated integrated backscatter values;
comparing the calculated variance value with a predetermined threshold value; and
judging that the examinee is a lipid rich plaque when the variance value is greater than the predetermined threshold value.

17. The method according to claim 16, further comprising:
displaying a B-mode image of the examinee which is generated based on the radio-frequency signals; and
setting regions of interest at given positions in the displayed B-mode image;

the time regions being determined depending on positions of the regions of interest.

18. The method according to claim 17, wherein the setting of the regions of interest comprises:
   setting a plurality of lines specifying a direction in which to array the regions of interest in the B-mode image; and
   arraying the same number of regions of interest on each of the set lines.

19. The method according to claim 18, wherein each of the radio-frequency signals includes a signal produced when an ultrasonic transducer mounted on a catheter makes a radial scan in the examinee, and the setting of the plurality of lines comprises setting the lines as equally spaced radial lines from a central position of the catheter in the B-mode image.

20. The method according to claim 19, wherein the setting of the plurality of lines comprises setting the lines at equally spaced intervals between two lines specified by a user and extending radially from the central position of the catheter in the B-mode image.

21. The method according to claim 19, wherein the arraying of the same number of regions of interest on each of the set lines comprises arraying the regions of interest at equally spaced intervals between two regions of interest specified by a user on each of the set lines.

22. A recording medium storing a control program for enabling a computer to perform a method according to claim 16.

23. A method of processing an ultrasonic signal comprising:
   scanning an examinee, which is a plaque in a blood vessel, by an ultrasonic wave;
   extracting radio-frequency signals in predetermined time regions respectively from a plurality of radio-frequency signals which are produced by the scanning of the examinee by an ultrasonic wave;
   calculating respective integrated backscatter values in the time regions;
   calculating linear averages of the calculated integrated backscatter values in integrated backscatter value groups with respect to mutually related time regions;
   calculating a variance value of an additive averages of the calculated integrated backscatter values;
   comparing the calculated variance value with a predetermined threshold value; and
   judging that the examinee is a lipid rich plaque when the variance value is greater than the predetermined threshold value.

24. The method according to claim 23, further comprising:
   displaying a B-mode image of the examinee which is generated based on the radio-frequency signals; and
   setting regions of interest at given positions in the displayed B-mode image;
   the time regions being determined depending on positions of the set regions of interest.

25. The method according to claim 24, wherein the setting of the regions of interest comprises:
   setting a plurality of lines specifying a direction in which to array regions of interest in the B-mode image; and
   arraying the same number of regions of interest on each of the set lines.

26. The method according to claim 25, wherein each of the radio-frequency signals includes a signal produced when an ultrasonic transducer mounted on a catheter makes a radial scan in the examinee, and the setting of the plurality of lines comprises setting the lines as equally spaced radial lines from a central position of the catheter in the B-mode image.

27. The method according to claim 26, wherein each of the mutually related time regions comprises a time region corresponding to a predetermined region of interest as counted from the central position of the catheter in the B-mode image on one of the lines.

28. The method according to claim 26, wherein the setting of the plurality of lines comprises setting the lines at equally spaced intervals between two lines specified by a user and extending radially from the central position of the catheter in the B-mode image.

29. The method according to claim 26, wherein the arraying of the same number of regions of interest on each of the set lines comprises arraying the regions of interest at equally spaced intervals between two regions of interest specified by a user on each of the set lines.

30. A recording medium storing a control program for enabling a computer to perform a method according to claim 23.

* * * * *